United States Patent [19]

Wehling et al.

[11] Patent Number: 5,219,574
[45] Date of Patent: Jun. 15, 1993

[54] MAGNESIUM CARBONATE AND OIL TABLETING AID AND FLAVORING ADDITIVE

[75] Inventors: Fred Wehling, New Hope; Steve Schuehle, Minneapolis; Navayanarao Madamala, Plymouth, all of Minn.

[73] Assignee: Cima Labs. Inc., Minneapolis, Minn.

[21] Appl. No.: 667,557

[22] Filed: Mar. 11, 1991

Related U.S. Application Data

[63] Continuation-in-part of Ser. No. 407,865, Sep. 15, 1989, abandoned.

[51] Int. Cl.⁵ .................................... A61K 9/20
[52] U.S. Cl. ..................... 424/464; 424/465; 424/489; 424/502; 424/682; 424/686; 514/960
[58] Field of Search ............... 424/464, 465, 466, 489, 424/498

[56] References Cited

U.S. PATENT DOCUMENTS

| | | | |
|---|---|---|---|
| 2,925,344 | 2/1960 | Peat | 99/140 |
| 3,404,011 | 10/1968 | Eolkin | 99/140 |
| 3,660,115 | 5/1972 | Revie | 99/140 R |
| 4,393,046 | 7/1983 | Baylis et al. | 424/117 |
| 4,409,202 | 10/1983 | Witzel et al. | 424/49 |
| 4,605,551 | 8/1986 | Buehler et al. | 424/682 |
| 4,609,543 | 9/1986 | Morris et al. | 424/440 |
| 4,954,349 | 9/1990 | Sheth et al. | 424/464 |

FOREIGN PATENT DOCUMENTS

0296118 12/1988 European Pat. Off.
606519 11/1934 Fed. Rep. of Germany.
5597844 6/1982 Japan.

OTHER PUBLICATIONS

Boylan J. C. et al. "Handbook of Pharmaceutical Excipients".
Patent Abstracts of JP57023691.
The Condensed Chemical Dictionary, Seventh Edition, 1966, p. 378.

Primary Examiner—Thurman K. Page
Assistant Examiner—James M. Spear
Attorney, Agent, or Firm—Lerner, David, Littenberg, Krumholz & Mentlik

[57] ABSTRACT

A tableting aid including magnesium carbonate and an oil adsorbed thereon provides useful lubricating and disintegration properties. A free-flowing particulate flavoring additive including magnesium carbonate and a flavor oil adsorbed thereon, is also described.

9 Claims, 4 Drawing Sheets

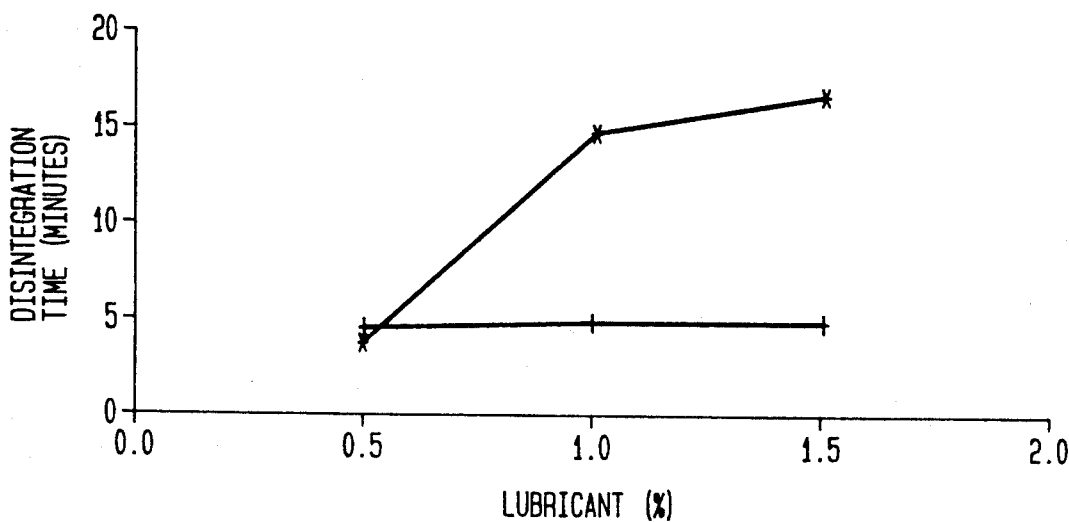

FIG. 1
EFFECT OF LUBRICANT CONCENTRATION ON DISINTEGRATION TIME OF DIRECTLY COMPRESSIBLE CALCIUM CARBONATE

TAB WT. = 1.40 GMS. EQUAL COMPACTION FORCE
5 MINUTE BLEND - 6 TAB AVE. 0.1N HCL 37C
—o— MAG STEARATE DISIN. TIMES > 60 MIN.

—o— MAG STEARATE
—+— TA
—*— LUBRITAB

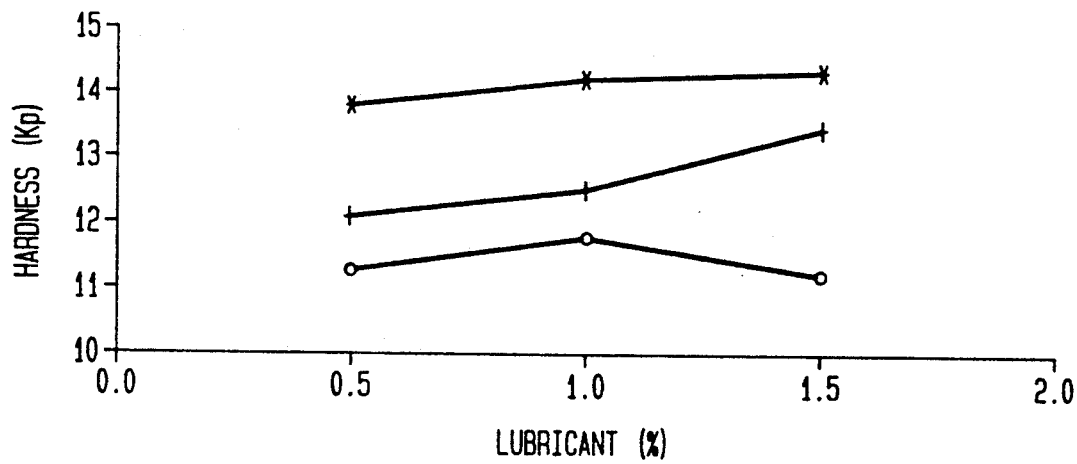

FIG. 2
EFFECT OF LUBRICANT CONCENTRATION ON HARDNESS OF DIRECTLY COMPRESSIBLE CALCIUM CARBONATE

TABLET WT. = 1.40 GM. 20 TAB. AVERAGE
5 MINUTE BLEND
EQUAL COMPACTION FORCE

—o— MAG STEARATE
—+— TA
—*— LUBRITAB

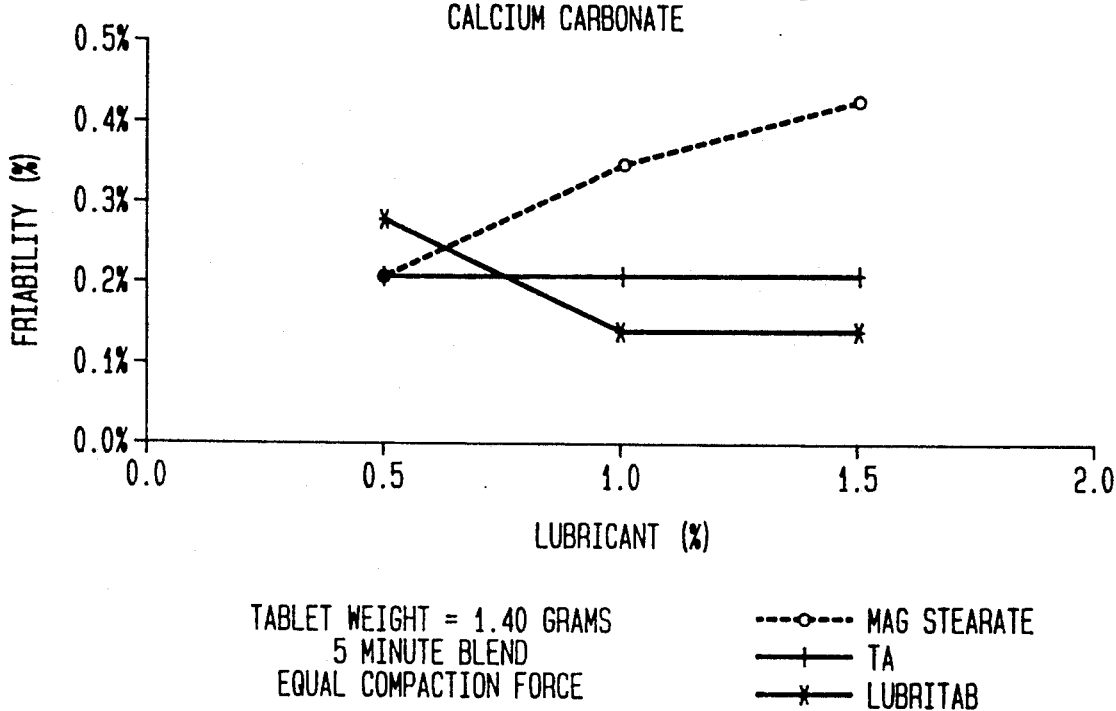

FIG. 3
EFFECT OF LUBRICANT CONCENTRATION ON FRIABILITY OF DIRECTLY COMPRESSIBLE CALCIUM CARBONATE

TABLET WEIGHT = 1.40 GRAMS
5 MINUTE BLEND
EQUAL COMPACTION FORCE

---o--- MAG STEARATE
———+——— TA
———*——— LUBRITAB

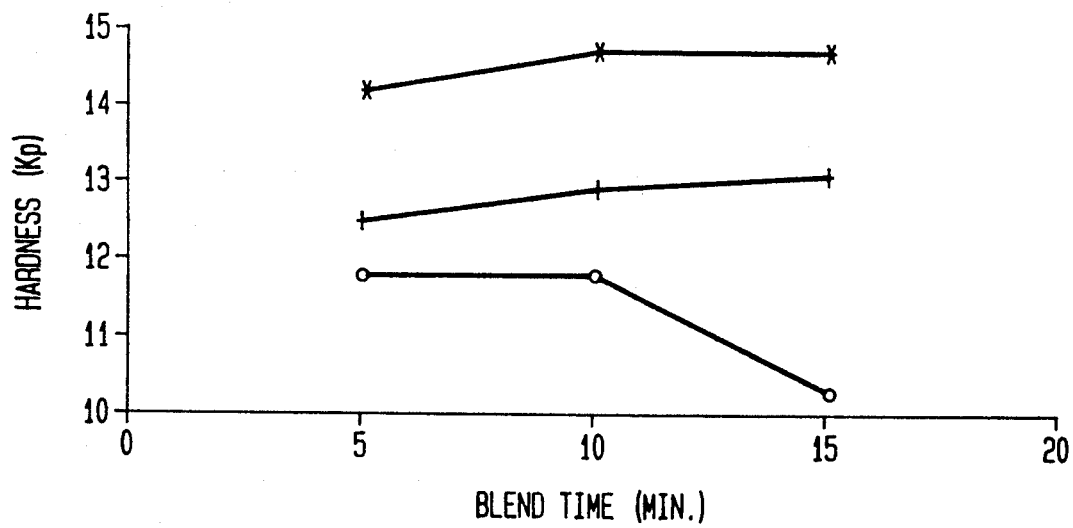

FIG. 4
EFFECT OF LUBRICANT BLENDING TIME ON HARDNESS OF DIRECTLY COMPRESSIBLE CALCIUM CARBONATE

TABLET WT = 1.40 GM. 20 TAB. AVERAGE
LUBRICANT CONCENTRATION = 1.0 %
EQUAL COMPACTION FORCE

———o——— MAG STEARATE
———+——— TA
———*——— LUBRITAB

EFFECT OF LUBRICANT BLENDING TIME ON DISINTEGRATION TIME OF DIRECTLY COMPRESSIBLE CALCIUM CARBONATE

TAB WT. = 1.40 GMS. EQUAL COMPACTION FORCE
1.0% LUBE CONC. 6 TAB AVE 0.1N HCL 37C
---o--- MAG STEARATE DISINT. TIMES ALL > 60 MIN.
---o--- MAG STEARATE
---+--- TA
---*--- LUBRITAB

EFFECT OF TA ON DISINTEGRATION TIME OF DIRECTLY COMPRESSIBLE $CaCO_3$
(USING 0.5% MAGNESIUM STEARATE)

5 MIN. MIX TIME
TABLET HARDNESS = +20 KP

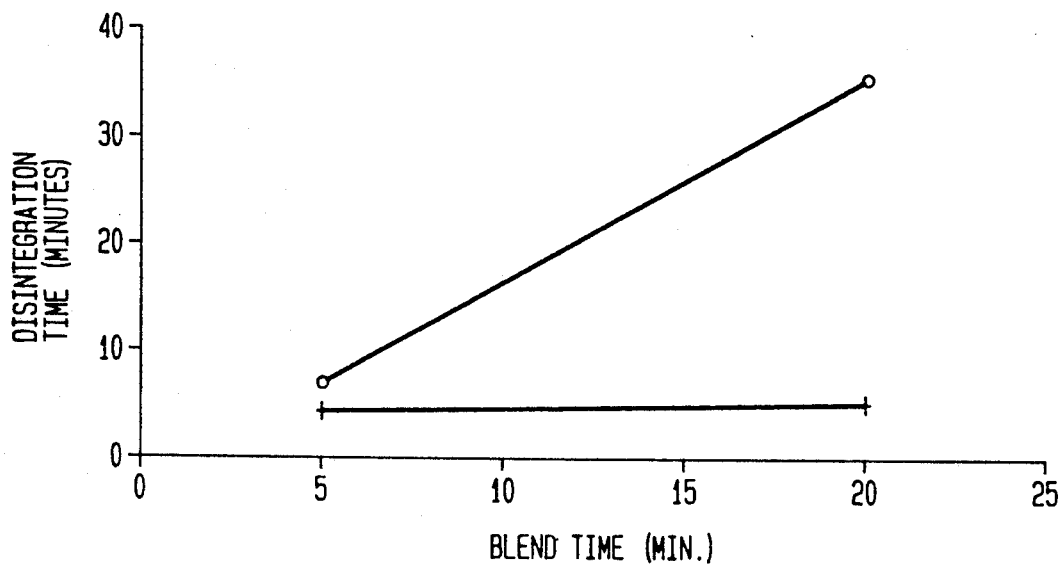

FIG. 7
EFFECT OF LUBRICANT BLENDING TIME ON
DISINTEGRATION TIME OF AVICEL* TABLETS

* AVICEL IS A REGISTERED TRADEMARK OF FMC
TAB WT = 505 MG. EQUAL COMPACTION FORCE
1.0% LUBE CONCENTRATION, 37 C DIST. $H_2O$

—o— MAG STEARATE
—+— TA

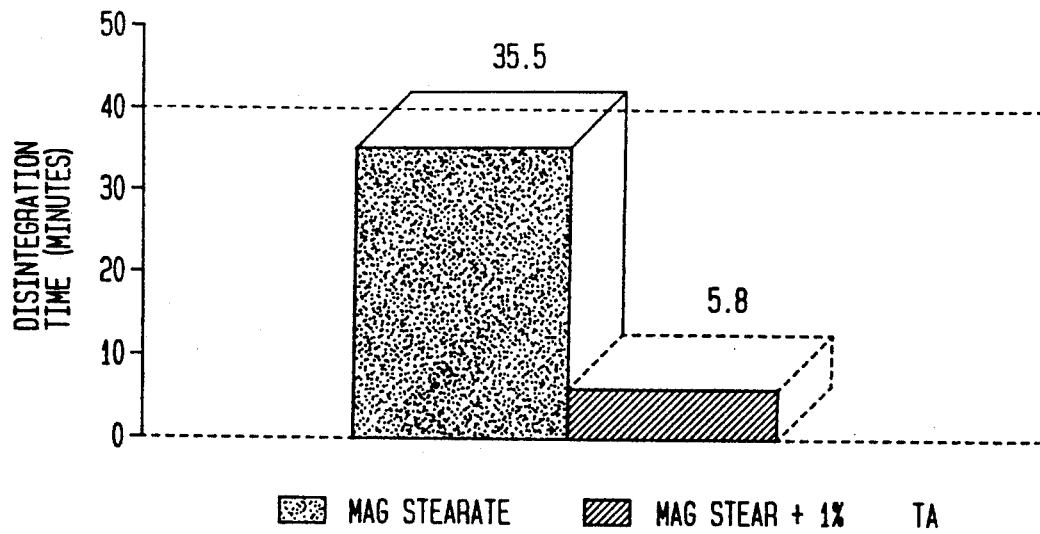

FIG. 8
EFFECT OF TA ON DISINTEGRATION
TIME OF AVICEL* TABLETS
(USING 1.0% MAGNESIUM STEARATE)

MAG STEARATE     MAG STEAR + 1% TA

* AVICEL IS A REGISTERED TRADEMARK OF FMC
TAB WT = 510 MG. EQUAL COMPACTION FORCE
20 MIN. MIX TIME, 37 C DIST. $H_2O$

MAGNESIUM CARBONATE AND OIL TABLETING AID AND FLAVORING ADDITIVE

This application is a continuation-in-part of Wehling, et al. Ser. No. 407,865, filed Sep. 15, 1989, now abandoned, the disclosure of which is hereby incorporated by reference.

TECHNICAL FIELD

The present invention relates to the field of tableting aids and specifically tableting lubricants and disintegrants.

BACKGROUND OF THE INVENTION

One of the most common dosage forms for pharmaceuticals is the tablet. However, tablets are not limited to pharmaceuticals and have been applied in areas as diverse as detergents, beverages and sweeteners. Tablets are successful devices for delivering intended ingredients because of their wide consumer acceptance, convenience, ease of use and economy. In common tableting processes, material which is to be tableted is deposited into a cavity, and one or more punch members are then advanced into the cavity and brought into intimate contact with the material to be pressed, whereupon compressive force is applied. The material is thus forced into conformity with the shape of the punches and the cavity. Hundreds, and even thousands, of tablets per minute can be produced in this fashion. Various tableting methods, well known to those skilled in the art, are comprehensively discussed in Lieberman, *Pharmaceutical Dosage Forms: Tablets Volume* 1, Second Edition, Revised and Expanded Copyright 1989 by Marcel Dekker, Inc.

These basic compression steps are common to most tableting operations including methods known as direct dry compression, wet granulation, and dry granulation. See European patent application 0,127,400.

The term "direct compression" was historically used to describe compression of a single crystalline compound into a compact tablet form without the use of additional ingredients. However, few compounds posses the necessary properties to make such compaction possible. The term has more recently evolved such that it now defines processes by which tablets are compressed directly from powder blends of active or intended ingredients and suitable excipients.

Where direct compaction is not possible, granulation techniques may also be used as a pre-treatment. Most powders cannot be compressed directly into tablets because they lack the proper characteristics. These characteristics include a lack of *compressibility and a lack of necessary lubrication. See Lieberman, supra at page 148. For these reasons materials to be delivered are often pretreated either alone or in combination with other fillers to form granules that readily lend themselves to tableting. This process is known as granulation. As commonly defined, "granulation" is any process of size enlargement whereby small particles are gathered together into larger, permanent aggregates to yield a free-flowing composition having a consistency similar to that of dry sand. This may be accomplished by agitation in mixing equipment or by compaction, extrusion or globulation. In granulation, active or intended ingredients are generally admixed with a compression vehicle. The compression vehicle or filler must have good compressibility, good flowability and stability under normal ambient conditions as well as being low in cost and satisfactory in both texture and appearance. In addition to compression vehicles, tablet formulations typically include other additives such as diluents, flavors, colors disintegrating agents and lubricants, all of which may be added during granulation or thereafter.

Lubricant, as used herein, refers to a material which can reduce the friction between the tablet, the die walls and the punch faces, which occurs during the compression and ejection of a tablet. Lubricants, in general, prevent sticking of tablet material to the punch faces and die walls. The term "antiadherents" is sometimes used to refer to substances which in some formulations are needed to aid the lubricant and prevent films from forming on the punch faces. However, as used in the present disclosure, the term "lubricant" is used generically and includes "antiadherents". Tablet sticking during formation and/or ejection may pose serious production problems such as reduced efficiency, irregularly formed tablets, and non-uniform distribution of intended agents or intended ingredients to be delivered thereby. These problems are particularly severe with high speed tableting approaches and methods.

Lubricants may be intrinsic or extrinsic. A lubricant which is directly applied to the tableting tool surface in the form of a film, as by spraying onto the die cavity and/or punch surfaces, is known as an extrinsic lubricant. Although extrinsic lubricants can provide effective lubrication, their use requires complex application equipment and methods which add cost and reduce productivity. Therefore, extrinsic lubricants generally are considered to be undesirable. See Leal, et al., U.S. Pat. No. 3,042,531 which describes another form of extrinsic lubrication by disclosing the compression of a lubricant tablet just prior to the tableting of the desired composition. After compaction of the lubricant tablet, a lubricated residue remains in the punch and cavity walls such that a subsequent tablet is lubricated. This obviously cuts tableting efficiency in half, raises cost and yields unwanted waste; namely the lubricant tablets.

Intrinsic lubricants are incorporated in the material to be tableted. Magnesium, calcium and zinc stearates and stearic acid have long been regarded as the most efficient intrinsic lubricants in common use. Concentrations of 0.3% to 2.0% are usually effective. Unfortunately, metallic stearates and stearic acid are not water soluble. This fact can seriously hinder tablet disintegration. Additionally, when these materials are used in products which are reconstituted into a solution prior to use, they leave an objectionable "scum" on the surface of the resulting solution.

To attempt to remedy this situation, a number of water soluble or water dispersible lubricants may be used. Unfortunately what these substances gain in water solubility, they sacrifice in lubrication efficiency. Other traditional intrinsic lubricants include hydrogenated and partially hydrogenated vegetable oils, animal fats, polyethyleneglycol, polyoxyethylene monostearate, talc, light mineral oils, sodium benzoate, sodium lauryl sulphate, and the like. See European Patent Application No. 0,275,834, the disclosure of which is incorporated by reference. See also Leal et al., U.S. Pat. No. 3,042,531.

Lubricants can be particularly important when compounding an effervescent tablet. According to the aforementioned Lieberman text, effervescent tablets could not be produced on high speed equipment without a suitable lubricant. Effervescent granulations are inherently difficult to lubricate partly because of the nature of the raw materials used and partly because of the requirement for rapid disintegration of the tablet. Typical intrinsic lubricants sacrifice either lubrication efficiency or desirable disintegration properties.

For example, while magnesium stearate used in conventional amounts is an effective lubricant, it may actually retard disintegration. This is not a generally insurmountable problem in effervescent formulations because of the disintegrating action of the effervescents. It may, however, slow disintegration sufficiently to reduce the commercial appeal of a tablet so formulated. Furthermore, where larger quantities of lubricant are required by the difficulty of tableting certain ingredients, the long disintegration time caused by the lubricant may become significant.

The retardation of disintegration caused by conventional lubricants is a particularly severe problem with non-effervescent tablets. Disintegration in the non-effervescent context generally refers to the break up of a tablet after administration. Obviously, the success of, for example, a drug may depend upon its complete and controlled administration. However, lubricants and disintegrants generally functionally oppose each other. See Lieberman, supra at pg. 108. In fact, conventional disintegrants possess binding and or adhesive properties which inhibit the lubrication efficiency of a lubricant.

Thus, it is a difficult task to produce a tablet formulation which will dissolve and disintegrate in a controlled and timely fashion, but which can be lubricated sufficiently to render high speed manufacturing possible.

An additional problem often encountered in forming a tablet is the inclusion of flavor. Flavors may be added in an attempt to mask objectionable tastes, or merely to make the taking the medicine more pleasurable. Doran et al., U.S. Pat. No. 4,352,821 is directed to a flavored compressible tableting agent formed from fructose and a carrier therefore. The carrier is preferably an edible substantially water insoluble inorganic salt and may include tri-calcium phosphate, di-calcium phosphate anhydrous, magnesium carbonate and mixtures thereof.

Similarly, in European Patent Application 0,275,834, the continuous process for the production of a comestible tablet is disclosed which comprises continuously contacting different ingredients together at high shear while atomizing a solvent of at least one ingredient into the mix. The atomized solvent may include water soluble sweetening agents, water soluble artificial sweetening agents, dipeptide base sweeteners and mixtures thereof.

Levin, U.S. Pat. No. 2,147,743 discloses the use of normal magnesium carbonate and a fruit acid to provide a dry effervescent composition. In one embodiment, a lemon oil flavoring is blended with the dry powder incorporating a minor amount of magnesium carbonate together with sugar and citric acid. This is said to yield a non-caking powder.

As the references cited herein indicate, no single solution to the problems discussed has been completely satisfactory. In fact, despite all of the attention devoted to tableting lubricants and tableting disintegrants in the prior art, there still remains a need and a strong desire amongst those in the tableting industry for a dry free-flowing tableting aid which overcomes or mitigates the disadvantages of the lubricants discussed above.

In particular, there is a need for a dry free-flowing tableting aid which provides suitable lubrication while tableting, which is water dispersible, and which does not have a substantial adverse effect on the compaction process or upon disintegration and dissolution times.

There is a further need for enhanced methods and materials for flavoring tablets.

The need for enhanced methods and materials for flavoring is not, however, limited to tablets. Flavor oils are widely used to flavor consumable products such as foods and beverages, and even other pharmaceutical dosage forms. Unfortunately, flavor oils are generally difficult to incorporate into these consumable products directly, and therefore must generally be spray-dried onto carriers such as dextrose, mannitol or other sugars to form fine, flowable powders. These fine powders can then be easily handled and incorporated as needed.

Unfortunately, spray-drying is not a completely satisfactory technique. Some flavor oils, for example, are very volatile and the spray-drying of these flavor oils generally results in a high oil loss rate. This dramatically effects the cost of the finished product. Furthermore, additives are also required to facilitate the spray-drying process such as antioxidants which are commonly added to preserve the integrity of the spray-dried flavor oil.

Another problem with regard to delivery of flavor oils is the carrier. Sugars may be used, however, the added caloric value of the sugar may render these flavor carriers unattractive for numerous applications. This is particularly true when attempting to market consumable products to today's more health-conscious consumers. Other carriers could be envisioned such as those described in Gioffre, et al., U.S. Pat. No. 4,818,518. Specifically, Gioffre, et al. suggests the mixing of a flavored oil with solid particulate carrier materials such as starch, calcium carbonate, paraffin, vegetable wax, fat, or higher fatty acids. However, even these potential carrier substances are not without problems. For example, calcium carbonate can only handle a rather low loading factor of flavored oil. Furthermore, calcium carbonate, for example, when coated with about 11 weight percent flavored oil, produces a clumpy agglomerate which is not free-flowing and, therefore, difficult to use and to homogeneously incorporate into products.

Therefore, there remains a need for improved flavor delivering agents in general, for more efficient methods of manufacturing these materials and for their use.

SUMMARY OF THE INVENTION

One aspect of the present invention provides a dry particulate tableting aid comprising a particulate magnesium carbonate having adsorbed thereon at least one oil, the oil being added to the magnesium carbonate in an amount effective to produce a free-flowing, dry, particulate tablet aid.

In a most preferred embodiment of the present invention, the oil is safe for mammalian consumption.

Desirably, the ratio of oil to magnesium carbonate by weight is at least about 0.15:1, more desirably between about 0.15:1 and about 0.6:1, and most preferably between about 0.25:1 and about 0.45:1.

This aspect of the invention incorporates the discovery that magnesium carbonate can adsorb a relatively large amount of oil and still remain a dry, free-flowing particulate material having lubrication and disintegration properties. Magnesium carbonate has oil take-up and retention properties superior to those of chemically related compounds. Because the aid, according to this aspect of the present invention, is a free-flowing, particulate material, it can be incorporated into particulate tableting compositions, and uniformly distributed throughout the composition by dry blending using conventional equipment and techniques. Further, the preferred aids according to the invention are readily dispersible in water and neither produce an undesirable "scum" nor materially retard tablet disintegration while providing an effective degree of lubrication. The dry tableting aid in its preferred forms, is exceptionally effective in tableting processes. Thus, minor amounts of the preferred tableting aids according to this aspect of the invention, when incorporated in a tableting composition, will provide effective intrinsic lubrication. The minor amount of tableting aid will also facilitate the controlled disintegration of tablet formulated therewith. Furthermore, according to this aspect of the present invention, a relatively large amount of the tableting aid may be incorporated into a tablet to further facilitate the disintegration of the tablet, without adverse effects to either lubrication efficiency, or the normal problems attendant the use of higher weight percents of a lubricant.

Preferred tableting aids according to this aspect of the invention are sodium and sugar free. Moreover, because the components of the preferred tableting aids of the present invention are readily available in bulk, they can be produced effectively at low cost effective.

According to a further aspect of the invention, the oil may be a flavored oil. The tableting aid thus serves as a flavoring as well, and eliminates the need for a separate flavoring. In this case, the oil serves both as a part of the lubricant/disintegrant and as a carrier for oil-soluble flavor components.

A further aspect of the invention provides a composition of matter comprising a particulate tableting aid as aforesaid, including magnesium carbonate and a flavored or non-flavored oil, and an effective amount of at least one intended ingredient.

The intended ingredient may be a pharmaceutically active ingredient, and may be present in a pharmaceutically effective amount. The composition may further include one or more additional adjuvants selected from the group consisting of flavors, diluents, colors, binders, fillers, additional disintegration agents and lubrication and effervescent agents. Compositions incorporating an effervescent agent are particularly preferred.

The compositions of the present invention are also useful for providing flavor to consumable products other than tablets. Therefore, one aspect of the present invention is the provision of a flavoring additive which includes particulate magnesium carbonate having adsorbed thereon at least about 20 weight percent, based upon the weight of the magnesium carbonate, of at least one flavor oil. In a preferred embodiment, the amount of flavor oil ranges from about 20 to about 55%, and more preferably, from about 30 to about 45 weight percent based upon the weight of the magnesium carbonate.

The resulting flavoring additive has several advantages. First, magnesium carbonate is able to adsorb and therefore deliver a much higher load of flavor oil to, for example, an edible foodstuff, than other carriers such as calcium carbonate. The flavoring additives of the present invention can therefore be used in lower quantity to provide the same level of flavoring. As such, the use of the compositions of the present invention can represent a great savings in weight and size of the final product and cost of raw materials. These compositions can also provide a significantly higher degree of flavor in environments where weight, size, or other properties would preclude the use of larger quantities of other, less efficient materials. Furthermore, because the compositions of the present invention remain in a discreet, free-flowing particulate form, they may be more easily manipulated and combined with, for example, edible foodstuffs.

The present invention also relates to methods of making a free-flowing particulate flavoring additive. These additives may be made by providing a particulate magnesium carbonate, providing a flavor oil in an amount of between about 20 and about 55% by weight of the magnesium carbonate, and mixing the magnesium carbonate and the flavor oil such that the flavor oil is substantially completely adsorbed on the magnesium carbonate. The use of magnesium carbonate as a carrier for a flavor oil not only allows for the elimination of the need for spray-drying and all of its drawbacks, but also allows for the incorporation of significant amounts of flavor oil. Therefore, the present invention provides a convenient, efficient and effective way to produce flavoring additives having high loads of flavor.

The present invention is also directed to a flavored consumable article which is, at least partially, flavored by the flavoring additives of the present invention. The flavoring additives of the present invention are provided in an amount sufficient to provide at least a portion of the flavor of the article. That is to say the flavoring additive may provide the entire flavor of the article, may alter the natural flavor of the article by adding additional flavors, augment an identical naturally occurring flavor, or may mask objectionable naturally occurring flavor. The "consumable" article generally includes an edible foodstuff which may include solid foods, partially liquid foods, or beverages. The present invention also relates to a method of flavoring a consumable article by providing an edible foodstuff in need of flavoring and intermixing at least a portion of the edible foodstuff with the flavoring additive of the present invention provided in an amount sufficient to provide at least a portion of the flavor of the article. The consumable articles produced thereby have several advantages. For example, at the same size and weight, a significantly greater amount of flavor oil can be delivered to an edible foodstuff. Therefore, the taste of the resulting consumable product may be enhanced.

Furthermore, it may be possible to provide superior texture by eliminating a percentage of flavoring additive necessary to provide a specific level of flavor. Also, since magnesium carbonate is generally non-caloric, the flavoring additives of the present invention may be particularly useful for the preparation of dietetic and/or diabetic foodstuffs.

Still further aspects of the present invention provide a process of producing a tablet comprising the step of forming a tablet by the application of compressive force to a tableting composition as aforesaid, and tablets made by such process These and other objects of the invention will be more readily apparent from the detailed description of the preferred embodiment set forth below.

BRIEF DESCRIPTION OF THE DRAWINGS

FIG. 1 is a graphical representation of the effect of lubrication concentration on disintegration time of directly compressible calcium carbonate.

FIG. 2 is a graphical representation of the effect of lubricant concentration on hardness of directly compressible calcium carbonate.

FIG. 3 is a graphical representation of the effect of lubricant concentration on the friability of directly compressible calcium carbonate.

FIG. 4 is a graphical representation of the effect of lubricant blending time on the hardness of directly compressible calcium carbonate.

FIG. 7 is a diagramatic representation of the effect of lubricant blending time on the disintegration time of AVICEL tablets.

FIG. 8 is a graphical representation of the effect of the tableting aid, also referred to as TA, on the disintegration time of AVICEL tablets containing 1.0 percent magnesium stearate.

DETAILED DESCRIPTION OF THE PREFERRED EMBODIMENT

Figure 5:
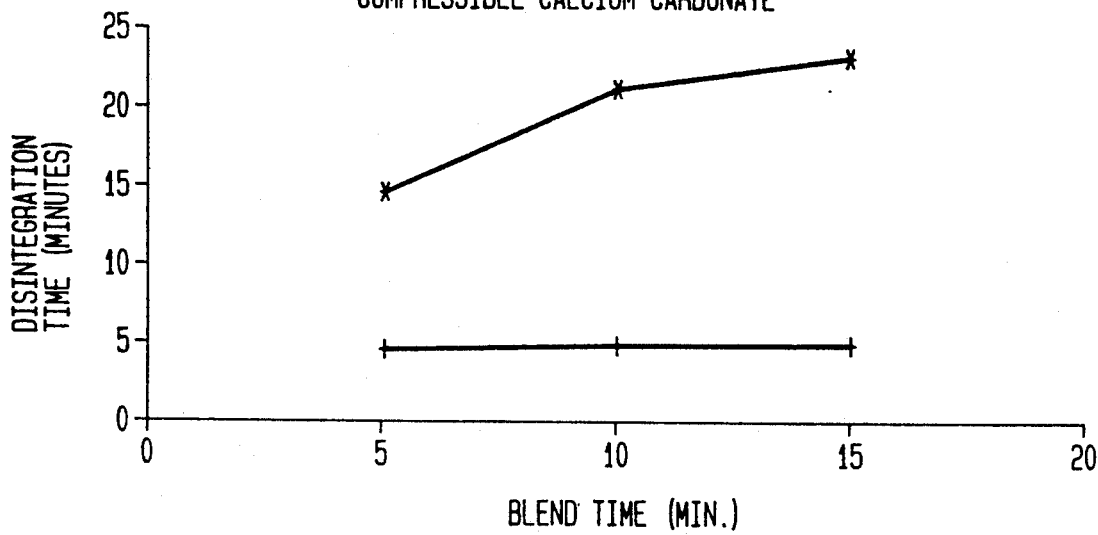
FIG. 5 is a diagramatic representation of the effect of lubricant blending time on disintegration time of directly compressible calcium carbonate.

The particulate tableting aid according to one embodiment of the present invention includes magnesium carbonate and an oil. The magnesium carbonate may be commonly available in bulk particulate form from a number of manufacturers. Where the tableting aid is to be employed in a comestible or pharmaceutical tablet, food or pharmaceutical grade magnesium carbonate should be employed. The specific parameters of comestible magnesium carbonate may be obtained by reference to the United States Pharmacopoeia, the pertinent portions of which are hereby incorporated by reference. So-called "heavy" magnesium carbonate is particularly preferred. However, light grade magnesium carbonate may also be used. The particulate magnesium carbonate may have a particle size such that at least 90 percent of the particulate will pass through a 325 mesh screen. In a preferred embodiment, heavy magnesium carbonate is used having a particle size such that between about 97 to about 99 percent of the particulate will pass through a 325 mesh screen. Generally, heavy magnesium carbonate has a loose bulk density of between about 10 and about 14 lbs./cu.ft. Light magnesium carbonate which is also useful in the practice of the present invention will generally have a size such that about 99 percent of the particulate will pass through a 325 mesh screen. The loose bulk density of light magnesium carbonate is generally between about 5 and 8 lbs./cu.ft. Of course the terms by particulate, particle, etc., it is understood that any particle, grain, granule or powder is contemplated.

As used in this disclosure, the term "oil" refers to a liquid having lubricating properties. Preferably, the oil is an organic liquid. The most common organic oils include mineral oils, which consist essentially of paraffins and/or hydrocarbons, and vegetable and animal oils, which consist essentially of triglycerides. Essentially any oil may be utilized in a tableting aid according to the present invention. Where the tableting aid is to be used in making a pharmaceutical or comestible tablet, the oil is desirably safe for mammalian consumption.

The oil may be either flavored or non-flavored. Although many oils have some weak, incidental flavor or aroma, the term "flavored" and "non-flavored" are used with reference to oil in the ordinary sense of those terms. Thus, as referred to in this disclosure a "flavored oil" is one which has a strong, readily perceptible taste or aroma and which is capable of imparting such taste and/or aroma to other ingredients when a minor proportion of the oil is mixed with such other ingredients.

The preferred non-flavored oils for use in tableting aids according to this embodiment of the invention include mineral oils of the type known in the trade as white mineral oil, soy bean oil and other vegetable oils.

The flavored oils which may be utilized according to the present invention generally include volatile flavor and/or aroma ingredients in an oily base or carrier. The oily base or carrier may be derived from the same or different source as the flavor and/or aroma ingredients. For example, citrus oils such as lemon oil, orange oil and the like generally include natural volatile ingredients of the citrus fruit together with an oily carrier likewise derived from the citrus fruit. Other flavored oils which may be utilized according to the present invention include mixtures of natural or artificial flavoring and aroma imparting ingredients in a mineral or vegetable oil base. The term "fold" may be employed to describe the strength of the flavorants or aromas in a flavored oil, and particularly in naturally derived flavored oil. As used herein, description of a flavored oil as "N-fold" should be understood as meaning that the oil contains N times as much of the most significant flavor or aroma ingredients per unit volume compared to the naturally occurring flavored oil. As will be appreciated, higher fold oils are more concentrated and hence are more flavorful and aromatic. In a preferred embodiment, the flavored oils are selected from the group consisting of citrus extracts, fruit extracts (non-citrus), and plant extracts, and mixtures thereof.

The preferred mineral oils, for use in the present invention have a viscosity of between about 10 and about 100 and more preferably about 30 to about 75 centistokes at 40° C. The preferred mineral oils for use in the present invention have a specific gravity typically between about 0.84 and about 0.88. In a particular preferred embodiment of the present invention, a specific gravity of about 0.87. Typical triglyceride-based oils have specific gravity of between about 0.90 and 0.92.

The ratio of oil to magnesium carbonate should be as high as possible consistent with maintenance of a dry, free-flowing powdery consistency in the tableting aid. The ratio of oil to magnesium carbonate on a volume to weight basis (milliliters of oil to grams of magnesium carbonate) desirably is at least about 0.2 to about 0.6, preferably about 0.3 to about 0.5 and most preferably about 0.4. With oils having the aforementioned specific gravities, the ratio of oil to magnesium carbonate by weight may be at least about 0.15, more desirably about 0.15 to about 0.6, more preferably about 0.25 to about 0.45, and most preferably about 0.36.

As should readily be appreciated, any oil soluble material may be carried by the oil and delivered as part of the tableting aid of the present invention.

The magnesium carbonate may be mixed with the oil using substantially any suitable mixer. Closed mixing vessels are preferred to avoid inadvertent loss of magnesium carbonate during the mixing process. The mixing procedure can be performed in closed mixers of the type commonly employed for vacuum granulation processes in the pharmaceutical industry, although no vacuum is normally applied during the mixing procedure.

Certain vacuum granulating mixers have an enclosed mixing vessel with a propeller rotatably mounted at the bottom of the vessel for stirring the contents, and a further, small propeller commonly referred to as a "chop" mounted on a small shaft adjacent the periphery of the vessel. The small shaft is provided with means for rotating it and also for sliding the shaft so as to move the chop up and down within the vessel, towards and away from the propeller. This form of mixer also has a spraying nozzle and a spray ingredient tank connected to that nozzle so that liquid ingredients can be introduced into the interior of the vessel while stirring proceeds.

Preferably, about 50 to about 90 percent and desirably about 60 to about 80 percent of the magnesium carbonate used in making the tableting aid is loaded into the vessel first, and the oil is added by discharging it from the spraying tank into the vessel while the propeller and chopper are operated to stir the vessel contents. After all of the oil has been added, the propeller and chopper are stopped, and the remainder of the magnesium carbonate is added and stirring is resumed using the propeller and chopper. It is not essential that the oil be introduced into the vessel as a spray. Even where the oil is discharged into the vessel as a stream, the mixing action, and the natural tendency of the oil to adsorb onto the magnesium carbonate ordinarily will result in good distribution of the oil onto the magnesium carbonate with reasonable mixing times, typically less than about I hour and usually less than about 15 minutes total mixing time.

A further aspect of the present invention provides a composition of matter which is formed by blending the particulate tableting aid previously described with at least one intended ingredient.

The term "intended ingredient(s)" should be understood as referring to an ingredient or ingredients which is capable of performing a function when a tablet containing the ingredient is used. The intended ingredients used in the present composition may include essentially any ingredients that can be provided as a tablet. In a tablet for use as a food or beverage, the intended ingredients may include specific flavors, nutrients and the like. It may also include soaps, detergents, surfactants, foaming agents, anti foaming agents, adsorption agents, dyes and the like. By the terms pharmaceutical or pharmaceutically active ingredients, however, the inventors do not wish to be bound to a definition which excludes delivery of medication to animals. Furthermore, for the purposes of this invention, the term "pharmaceutically active ingredient" is understood to include vitamins and minerals as well as other ingredients commonly regarded as nutritional supplements and combinations thereof. Other pharmaceutically active ingredients may include antacids, analgesics, anti-inflammatories, antibiotics, vitamins, minerals, laxatives, anorexics, antiasthmatics, antidiarrhetics, antiflatuents, antimigraine agents, antispasmodics, sedatives, antihyperactives, tranquilizers, antihistamine, decongestants, beta-blockers, antialcoholism agents, cough suppressants, fluoride supplements, antiseptics and combinations thereof.

The amounts of the intended ingredient or ingredients in the composition is selected according to conventional criteria associated with the individual ingredients. An effective amount of each intended ingredient is specifically contemplated. The term "effective amount", as used with reference to an intended ingredient, should be understood as referring to an amount of the intended ingredient sufficient that a tablet containing a reasonable amount of the composition will contain enough of the intended ingredient to perform the normal function of that ingredient. With respect to pharmaceuticals, a pharmaceutically effective amount is contemplated. A pharmaceutically effective amount is the amount or quantity of a drug, mineral or substance which is sufficient to elicit the required or desired therapeutic response.

This composition may also include one or more additional adjuvants which can be chosen from those known in the art including flavors, diluents, colors, binders, fillers, lubricants, disintegrants and effervescent agents. In a particularly preferred embodiment according to the present invention, the composition includes an effervescent agent.

Examples of binders which may prove useful according to the present invention are acacia, tragacanth, gelatin, starch, cellulose materials such as methyl cellulose and sodium carboxymethyl cellulose, alginic acids and salts thereof, magnesium aluminum silicate, polyethylene glycol, guar gum, polysaccharide acids, bentonites, sucrose, polyvinylpyrrolidone, microcrystalline cellulose, sorbitol, and the like. Binders may be used in an amount of about 5 to about 25 weight percent of the total composition.

Coloring agents may include titanium dioxide, dyes suitable for food such as those known as F.D.& C. dyes, etc.

Flavors incorporated in the composition apart from the tableting aid may be chosen from synthetic flavor oils and flavoring aromatics and/or oils, extracts from plants, leaves, flowers, fruits and so forth and combinations thereof. These may include cinnamon oil, oil of wintergreen, peppermint oils, clove oil, bay oil anise oil, eucalyptus, thyme oil, cedar leaf oil, oil of nutmeg, oil of sage, oil of bitter almonds and cassia oil. Also useful as flavors are vanilla, citrus oil including lemon, orange, grape, lime and grapefruit and fruit essences including apple, pear, peach, strawberry, raspberry, cherry, plum, pineapple, apricot and so forth. The amount of flavoring may depend on a number of factors, including the strength of the taste desired. Where the particulate tableting aid of the present invention includes a flavored oil, however, less additional flavorant need be incorporated in the composition apart from the aid. In a particularly preferred arrangement, the flavorant in the tableting aid constitutes essentially all, or at least the major portion of, the flavorant in the entire composition. Thus, incorporation of the flavorant in the tableting aid evades the need to add other flavorants. This is particularly advantageous as it is often difficult to dispense a conventional flavorant uniformly throughout a tableting composition.

Effervescent agents may include any combination of ingredients which will yield a gas when the tablet is employed. The most common effervescent agents, such as alkali bicarbonates or carbonates and food acids such as citric acid yield carbon dioxide upon contact with water. The magnesium carbonate in the lubricant, when combined with a suitable reactive acid may enhance the effervescent qualities of the effervescent composition produced thereby. Effervescent materials typically are present in amounts of up to 95 weight percent but preferably are present in an amount of from about 60 to 90 percent by weight of the final composition.

The resulting material is a dry, free-flowing particulate material. As used in this disclosure with reference to a particulate material, the term "dry" means material having no distinct, flowable liquid phase, thus, it is believed that there may be a microscopic coating of liquid oil overlying all surfaces of the magnesium carbonate particles. Any such microscopic liquid phase does not behave as liquid in that it is tightly adsorbed on the surfaces and does not exhibit any perceptible flow under ordinary conditions. Also, as used in this disclosure the term "free-flowing" refers to a particulate material which is substantially free of large lumps or aggregates and which can be poured. Desirably, free-flowing particulate materials exhibit an angle of repose less than about 50 degrees, so that when the particulate material is placed in a pile the surface of the pile will lie at an angle of less than about 50 degrees to the horizontal.

It has been surprisingly found that the tableting aids of the present invention may be advantageously used as a tableting lubricant and/or as a tableting disintegration agent. That is to say, the tableting aid of the present invention may serve either as lubricant or as disintegration agent, or as both simultaneously. This is surprising and unexpected in as much as the inclusion of even low levels of lubricant in conventional tablets generally retards disintegration of the tablet and because the inclusion of a disintegration agent generally promotes binding or adhesion which undercuts the effectiveness of the lubricant. Thus, the realization of a tableting aid which facilitates both lubrication and disintegration represents a great advance.

Furthermore, the number of factors controlling the release rate of the intended ingredient is reduced by using the tableting aid according to the invention instead of conventional lubricants and disintegrants, it is easier to control and "tailor" the release rate thereof.

The magnesium carbonate and oil aid discussed above may be present in the composition in relatively small amounts, typically about 1.5 percent by weight or less, and preferably about 1 percent by weight or less, particularly when used solely as an intrinsic lubricant. Most preferably, the tablet aid constitutes about 0.5 to about 0.8 percent by weight of the tableting composition.

When used as a disintegration agent or as both a lubricating agent and a disintegrant however, the tableting aid of the present invention may be present in significantly higher amounts, up to about 20 weight percent based on the weight of the total composition. However, in a preferred embodiment according to the present invention, between about 0.5 to about 10 percent by weight of the total composition may comprise the tableting aid of the present invention. In a more preferred embodiment, the tableting aid of the present invention may be present in an amount of between about 1.0 and about 5.0 percent by weight.

Because the tableting aid is a dry free-flowing particulate material, it can be blended with other particulate constituents by ordinary dry blending techniques, as by tumbling in a twin-shell blender. The dry free-flowing particulate tableting aid can be readily distributed with good uniformity throughout the tableting composition. The tableting composition may be subjected to granulated processes wherein the tableting composition is admixed with a minor proportion of liquids and the liquid is subsequently removed, leaving behind agglomerated granules. The so granulated composition can be subjected to conventional screening techniques to provide the desired particle size distribution according to conventional criteria. The tableting composition, with or without such an intermediate granulation step, may then be formed into tablet by compression using conventional tableting equipment. Ordinarily, the tableting equipment is arranged to fill a tubular die with the tableting composition and to advance a pair of closely fitting punches into the die to thereby compress the composition and form the tablet, where upon the finished tablet is ejected from the punch and die assembly.

Tableting aids according to the present invention provide excellent intrinsic lubrication. Thus, the tableting operation ordinarily proceeds without problems caused by friction between the tableting composition and the punches and/dies, and without difficulties posed by adhesion of the tableting composition to the punches and/or dies. There is ordinarily no need for extrinsic lubrication of the punches or dies. Moreover, the tableting lubricant does not appreciably impede formation of a strong, coherent tablet upon compaction in the punch and die assembly.

This is marked contrast to the action of many other common lubricants, such as stearates. Tableting compositions incorporating stearate intrinsic lubricants commonly exhibit sensitivity to "over mixing". Thus, such compositions have an optimum degree of mixing. If this optimum degree of mixing is exceeded during formulation of the composition, so as to intimately distribute the stearate throughout the composition, the resulting tablets generally are soft and weak.

As previously discussed herein, the tableting aid according to the present invention, when used as a tableting lubricant, ordinarily does not materially retard disintegration of the finished tablet. In fact, the tableting aid of the present invention actually facilitates disintegration even when used in amounts more common to lubricants. Thus, a tablet incorporating lubricants according to the preferred embodiments of the present invention, in the amounts required to provide effective lubricating action, ordinarily will disintegrate in substantially the same time or less time than a tablet which does not incorporate an intrinsic lubricant. By contrast, the stearate lubricants, when present in amounts effective to provide substantial intrinsic lubrication commonly retard disintegration of the finished tablet, particularly if the tableting composition has been mixed to more than the optimum degree.

Moreover, the present tableting aid, when utilized in the amount required for effective lubrication and or disintegration, is readily dispersible in water when the tablet is dissolved in water. Typically, the aid disperses without a visible trace and without formation of an objectionable film or "scum". This is of particular importance in the case of effervescent tablets intended to be dissolved in water. The reasons for this good dispersion performance are not fully understood. The oil incorporated in the aid ordinarily is insoluble in water. However, because the present tableting aids provide effective lubricating actions at extremely low concentrations in the tableting composition, there is ordinarily not enough oil present to result in a visible film or scum. Moreover, although the present invention is not limited by any theory of operation, it is believed that the oil when adsorbed on the magnesium carbonate, is held in the form of a microscopic film rather than in the form of globules or droplets. This effect may also aid in dispersion of the oil upon disintegration of the tablet.

When the tableting aid of the present invention is intended to be used as either a disintegrant alone, or as both a lubricant and a disintegrant, it should be present in an amount sufficient to provide for effective disintegration of a tablet into which it is incorporated. Thus, if it is desired that the tablet completely disintegrate in less than ten minutes, an amount of disintegrant effective to provide for a disintegration time of less than ten minutes is contemplated. It is only possible to accommodate the higher concentration requirements of disintegrants because the lubricating aspects of the tableting aid of the present invention do not present any added disintegration problems. The amount of the tableting aid of the present invention which is effective to provide desirable disintegration properties is invariably an amount sufficient to provide effective intrinsic lubrication.

It is understood, of course, that the tableting aid of the present invention may be combined with other conventional lubricants or disintegrants as desired. These may include, as lubricants, those compositions previously discussed herein.

Disintegrants include starches as corn starch, potato starch and modified starches thereof, sweeteners, clays, such as bentonite, micro-crystalline cellulose, alginates, gums such as agar, guar, locust bean, karaya, pectin and tragacanth. Also included are the so-called superdisintegrants including modified carboxymethyl cellulose, cross-linked polyvinylpyrrolidine and soy polysaccharides.

When so used, the total amount of the combination of tableting aid and lubricant or disintegrant used should not exceed the ranges provided hereby.

As previously discussed, it is also possible to use compositions of the present invention as flavoring additives to flavor consumable products other than tablets. The term "flavoring additive" as used herein is a composition which may be added to a consumable article to enhance, mask, change, or provide flavoring to that consumable article. Generally, flavoring additives in accordance with the present invention include a particulate magnesium carbonate having adsorbed thereon at least 20 weight percent, based on the weight of the magnesium carbonate, of at least one flavor oil. In a particularly preferred embodiment, the amount of flavor oil useful and adsorbed to the particulate magnesium carbonate ranges from between about 20 to about 55 weight percent, based on the weight of the magnesium carbonate and, more preferably, between about 30 to about 45 weight percent thereof. The flavoring additives in accordance with the present invention are not oily, thus retaining a highly discreet, free-flowing, particulate form. Of course, at higher loads of oil, i.e., over 50% of flavor oil by weight, the free-flowing nature of the additive may begin to be reduced. However, this may still be acceptable for certain applications.

Both the size and type of magnesium carbonate and the types of flavor oils which may be useful in accordance with the present invention have previously been described herein. It is preferred that the particle size of the magnesium carbonate used in accordance with this aspect of the present invention be such that 90% of a particulate will pass through a 325 mesh screen and, more preferably, about 97 to about 99% of a particulate will pass through the 325 mesh screen. Flavor oils which may be useful in accordance with the present invention include those identified in Kurt Bauer et al., "Common Fragrance and Flavor Materials", Verlagsgesellschaft mbH, (1985), the text of which is hereby incorporated by reference. In manufacturing the flavoring additives of the present invention, it is possible to use conventional vat mixers or other blending or agitative-type liquid/solid processors. It is important, however, that a sufficient quantity of the magnesium carbonate surface area be exposed to the flavor oil such that adsorption may be complete. It is preferred that the oil be added to the magnesium carbonate slowly and uniformly to aid the homogeneous adsorption thereof.

The flavoring additives of the present invention may be incorporated into consumable articles such as edible foodstuffs. The term "edible foodstuffs" in accordance with the present invention includes food and beverage, such a soda, juice, candy, bread and baked goods, meats, poultries or fish, food seasoning additives such as spices, frostings, eggs, dairy, and other prepared foodstuffs. The flavored consumable articles may be produced by intermixing at least a portion of the edible foodstuff with a sufficient amount of the flavoring additive provided at least a portion of the flavor to the article.

Generally, the amount of flavoring additive added to food or beverage ranges from about 0.01 to about 10.0 percent, based on the weight of the food composition. In other words, the amount of flavoring additive used in accordance with the present invention should be sufficient to provide between about 0.001 and about 5.0 percent of flavor oil, based upon the weight of the edible food composition. The amount however may be greater or lesser depending upon the flavoring strength of the flavor oil, the amount of flavor oil adsorbed on to the magnesium carbonate used, and the reason for incorporating the flavor. For example, if the flavoring additive is being used to mask a strongly objectionable flavor which is naturally occurring in a foodstuff, or if the additive is to provide the only source of flavor to the foodstuff, then the amount used will generally increase. If, however, the flavoring additive is only being used to augment a flavor, or to add a greater dimension thereto, a lessor amount may be used.

Instead of, or in addition to the use of a flavor oil, it may also be advantageous to use a fragrance oil. The amount of fragrance oil useful and the amount of flavor oil useful are substantially identical. Thus, the flavoring additive of the present invention may have any combination of flavor and/or fragrance oil, so long as the total oil content does not destroy the free-flowing nature of the additive.

The foregoing will be better understood with reference to the following examples. These examples are for the purposes of illustration. They are not to be considered limiting as to the scope and nature of the present invention.

EXAMPLE I 8.0 kilograms of magnesium carbonate (heavy, USP) were weighed. 2.780 kilograms of mineral oil (Amoco White Mineral Oil, 35 USP having a specific gravity of 0.871) were also measured. 6.0 kilograms of the magnesium carbonate were charged to a Roto 50-P processor and the entire quantity of mineral oil was placed into a solvent tank and pressurized there to 50 PSI. The spray nozzle used was a No. 6505 manufactured by Spraying Systems. The chop was lowered and the propeller of the Roto processor was switched on at 130 revolutions per minute (rpm). The chop was also started. Mineral oil was then sprayed into the processing tank from the solvent tank whereupon it came into intimate contact with the 6 kilograms of magnesium carbonate charged thereto. Spraying continued for 8 minutes after which the propeller and chop were stopped and the spray turned off. The remaining two kilograms of magnesium carbonate were then added to the processor, the lid closed and mixing continued at a propeller rate of 200 rpm with the chop down and on. After five minutes the chop and propeller were stopped. The contents of the processor were discharged into a properly tared container and the total net weight of the mix was determined (10.621 kilograms). After accounting for the actual weight of the lubricant and samples sent to quality control, the total mix yield was determined and compared to the theoretical premix yield with a result that 99.6% of theoretical yield was realized.

EXAMPLE II 10,000 grams of magnesium carbonate were also weighed as discussed above. 4,000 ml (3,470 grams) of mineral oil were also weighed. The roto processor was again charged with 6 kilograms of magnesium carbonate.

Mineral oil was charged to the solvent tank and adjusted to 50 PSI. The propeller speed was again 130 rpm and mineral oil was sprayed into the processor for a period of about 10 minutes before stopping the processor. The remaining 4 kilograms of magnesium carbonate were then added to the processor and the chopper was turned on and the propeller was set to a rate of 130 rpm for 5 minutes. The contents of the processor were again discharged and the yield recorded.

EXAMPLE III

Procedures similar to those discussed above were used in this example. However, Amoco USP-18 mineral oil (light), having a specific gravity of 0.863, a viscosity at 100° F. of 187 SUS, a viscosity, at 40° C. of 36.3 cSt and a viscosity index of 101 was used.

8.0 kilograms of magnesium carbonate were weighed as were 2.62 kilograms of the 18-USP oil. The 18-USP mineral oil was sprayed into the processor containing 6 kilograms of magnesium carbonate for a period of 4 minutes, followed by the addition of the remaining magnesium carbonate and mixing with the chopper on and the propeller set to 200 rpms for 5 minutes. The yield was 98.9% of theoretical.

EXAMPLE IV

The procedure for this example is identical to the procedure used above in Example III. However, instead of Amoco 18-USP, 100% soybean oil having a density of approximately 0.90 grams/cc was used. 8 kilograms of magnesium carbonate was weighed and 2.88 kilograms of soybean oil was used. The yield was 98.8%, of theoretical.

EXAMPLE V

Using a small kitchen mixer, 200 ml of oil, orange valencia 5-fold (lot number 16281) manufactured by Citrus and Allied Fragrance Co. were measured as were 500 grams of magnesium carbonate. 300 grams of the magnesium carbonate were charged to the mixer. The mixer was set to a low speed and the orange oil was slowly added to the magnesium carbonate. The ingredients were mixed for 10 minutes, after which the remaining 200 grams of magnesium carbonate was added and mixed for an additional five minutes. The mix was discharged and passed through an 8 mesh screen. The resulting particles were a fine, free-flowing powder. The addition of 100 mg of the mix to a glass of water resulted in a weak taste of orange.

EXAMPLE VI

A low sodium effervescent analgesic composition was prepared which included the dry, free-flowing, particulate tableting lubricant prepared in Example II above.

|  | T1 (mg/tab) | T2 (mg/tab) |
| --- | --- | --- |
| *Base #08029-LSI | 2536 | — |
| **Base #07149-NSI | — | 2550 |
| 80 Mesh Aspirin | 162.5 | 162.5 |
| 40 Mesh Aspirin | 162.5 | 162.5 |
| Chlorpheniramine maleate 2 mg sodium bicarbonate 100 mg | 109.3 | 109.3 |
| Sodium Carbonate (Anhydrous) | 60.0 | 60.0 |
| Orange Flavor | 30.0 | 30.0 |
| Aspartame | 30.0 | 30.0 |
| Phenylpropanolamine hydrochloride 15.3 mg | 15.3 | 15.3 |
| Beta-Carotene | 30.0 | 30.0 |
| ***Lubricant | 30.0 | 30.0 |
|  | 3.165 gms | 3.179 gms |

*Base #08029-LSI consists of a granulation of: magnesium carbonate, potassium bicarbonate, calcium carbonate, sodium bicarbonate, citric acid which is not self lubricating.
**Base #07149-NSI is a granulation consisting of: magnesium carbonate, potassium bicarbonate, calcium carbonate, citric acid to form an effervescent system which is not self lubricating.
***Heavy mineral oil (Amoco white mineral oil 35 USP)/magnesium carbonate (heavy) at a ratio of 0.25:1.0.

EXAMPLE VII

The compositions of EXAMPLE VI were formed into tablets by compression using conventional high speed rotary tableting equipment. Specifically, the tableting equipment is arranged to fill a tubular die with the tableting compositions of EXAMPLE VI. A pair of closely fitting punches are advanced into the die to thereby compress the compositions and form tablets thereby. The tablet is ejected from the punch and die assembly.

The composition of T1 tableted well and lubricated well. When deposited into a glass of water at room temperature, foam was generated. After one minute, the tablet floated to the surface and after two minutes, the tablet had completely dissolved. The taste was very good. There was no precipitate.

The composition of T2 tableted well and lubricated well. When deposited into a glass of water at room temperature, foam results. The tablet remained at the bottom of the glass and completely dissolved within about 90 seconds. The taste was excellent. In fact, the taste was better than the tablets formed from the composition, T1.

EXAMPLE VIII

A vitamin composition was prepared which included the dry, free-flowing, particulate tableting lubricant of the present invention.

|  | mg/tab | 2000 tabs (g) |
| --- | --- | --- |
| *Base #06209-1 | 3084.4 | 6169.0 |
| Ascorbic Acid | 575.0 | 1150.0 |
| Thiamine Mononitrate | 36.0 | 72.0 |
| Riboflavin | 34.5 | 69.0 |
| Niacinamide | 34.5 | 69.0 |
| B-12 1% In Mannitol | 3.60 | 7.2 |
| Folic Acid 10% Trit. | 4.40 | 8.8 |
| D-Cal Pantothenate | 39.0 | 78.0 |
| Biotin 1% Trit. | 3.90 | 7.8 |
| Paba (Chem Dynamics) | 0.0350 | 0.07 |

-continued

|  | mg/tab | 2000 tabs (g) |
|---|---|---|
| Choline (Chem Dynamics) | 0.0350 | 0.07 |
| Insitol (Chem Dynamics) | 0.0350 | 0.07 |
| L-Tryptophan | 30.0 | 60.0 |
| Aspartame | 30.0 | 60.00 |
| Orange flavor | 50.0 | 100.00 |
| 1% Beta Carotene | 30.0 | 60.0 |
| **Lube Mixture | 30.0 | 60.0 |
| Tablet Weight = | 3985.4 mg | |

*Base #06209-1 is a granulation consisting of: potassium bicarbonate, calcium carbonate, magnesium carbonate, citric acid to form an effervescent system which is not self lubricating.
**The lubricant mixture of Example VI was used.

All of the ingredients except the base, aspartame, the orange flavor, the beta-carotene and the lube mixture were screened through a 16 mesh sieve. The choline was ground with a mortar and pestle. These ingredients were then charged to a twin shell blender where they were mixed for 20 min. The base was added to a processor along with a blended vitamin pre-mix and processed for 20 min., with the propeller set at 20 rpms and with tilt, but without vacuum.

The remaining ingredients were then added to the processor and the mixture was further processed for 5 min. under the same conditions. This composition was then tableted as described above with regard to Example VII.

Well-formed tablets were made having a thickness of 0.220 inches and dissolved in about 2.5 min. in room temperature water. The taste was good, and the tablets were characterized by good hardness.

EXAMPLE IX

The following composition was prepared:

|  | mg/tab | 2000 tabs (g) |
|---|---|---|
| *Base | 2826.7 | 5653.4 |
| Vitamin E 50% CWS | 880.0 | 1760.0 |
| Aspartame | 30.0 | 60.0 |
| Orange 10x | 50.0 | 100.0 |
| 1% Beta Carotene | 30.0 | 60.0 |
| **Lubricant | 30.0 | 60.0 |
| Tablet Weight | 3846.7 mg | |

*Base is same as in Example VIII
**Lubricant is the same as in Example VI.

The Base and Vitamin E were added to a 50 liter processor and mixed with tilt, prop=20 rpm, No Vacuum, for 20 min. Next, the Aspartame was screened through a 10 mesh screen and, along with the lubricant, were mixed with the original mixture for 5 min. without vacuum and at a prop rate of 20 rpm.

The mixture was then discharged from the processor into a large bag. Finally, the Beta-Carotene and Orange flavor were added to the bag and all of the ingredients were thoroughly mixed.

The compositions were then tableted as in EXAMPLE VII. The resulting tablets were of good quality, however, due to the use of spray dried Vitamin E, the rate of disintegration was unacceptable for commercial purposes.

EXAMPLE X

The following is a comparative example of the relative ability to lubricate of a magnesium composition prepared in the manner according to the present invention. Specifically, the following tableting aids, not in accordance with the invention, were prepared:

Magnesium oxide (heavy)/mineral oil (MGOMO-2);
Magnesium oxide (light)/mineral oil (MGOMO-1);
Magnesium oxide (light)/orange oil (MGOOL-1).

MGOMO-1

300 grams of light magnesium oxide was charged to a small mixer and 139 grams of mineral oil was added. The ingredients were mixed for 10 minutes and were screened through a No. 20 mesh screen. The resulting mixture was replaced in the mixer and an additional 100 grams of magnesium oxide was added and mixed for 5 minutes.

MGOOL-1

300 grams of light magnesium oxide was placed in a mixer and 200 milliliters of five-fold Valencia orange oil (173.75 gm) was added and mixed for 10 minutes. An additional 200 grams of magnesium oxide was then added and mixed with the previous mixture for 5 minutes. The resulting mixture was passed through a 20 mesh screen.

MGOMO-2

300 grams of heavy magnesium oxide and 139 grams of mineral were added to a mixer and mixed for 10 minutes. An additional 100 grams of magnesium oxide was added to the mix. The mixture was blended for an additional 5 minutes. The resulting blend was passed through a No. 20 mesh screen.

The above magnesium oxide oil mixtures were then tested for lubricant efficiency.

| CALCIUM TRIAL-1 | Mg/Tab | 3000 Tabs (g) |
|---|---|---|
| *Lot 0576 calcium containing formulation | 3100 | 9300.00 |
| MGOOL-1 MgO/orange oil lube | 40 | 120.00 |
| Tablet Weight = | 3140.0 mg | |

The tablets produced had irregular edges and were generally poorly formed indicating insufficient lubrication ability.

| CALCIUM TRIAL-2 | Mg/Tab | 3000 Tabs (g) |
|---|---|---|
| *Lot 0576 calcium containing formulation | 3100 | 9300.00 |
| MGOMO-1 MgO/mineral oil lube | 40 | 120 |
| Tablet Weight = | 3.140 grams | |

Again the tablets had poorly formed edges and were poorly shaped indicative of poor lubrication.

| CALCIUM TRIAL-3 | Mg/Tab | 1500 Tabs (g) |
|---|---|---|
| *Lot 0581 calcium containing formulation | 3100 | 4650.00 |
| MGOMO-2 MgO/mineral oil lube | 40 | 60.00 |
| Tablet weight = | 3.140 grams | |

The tablet edges were not smooth. Lubrication was insufficient.

| CALCIUM TRIAL 4 | Mg/Tab | 3225 Tabs (g) |
|---|---|---|
| *Lot 0585 calcium containing formulation | 3100 | 10,000.00 |
| Lot 07209-LI** magnesium carbonate/oil lubricant | 50 | 161.25 |
| Tablet weight = |  | 3150 milligrams |

*The lots were production runs containing identical ingredients in identical proportions.
**Magnesium carbonate tableting aid formed in accordance with Example II.

Tablets' edges are far superior to those lubricated with magnesium oxide/oil even though edges are not perfectly smooth. The calcium containing mixture and the magnesium carbonate lubricant were only mixed for 5 minutes per each tableting. It is expected that a longer mixing time with magnesium carbonate could improve the overall tablet appearance.

EXAMPLE XI

With reference to FIG. 1 the effect of lubricant concentration on the disintegration time of directly compressible calcium carbonate was determined and is graphically represented. Tablets having a weight of 1.40 grams were produced by blending various concentrations of magnesium stearate, the tableting aid of the present invention or LUBRITAB brand tableting lubricant for 5 minutes with directly compressible calcium carbonate. LUBRITAB is hydrogenated vegetable oil available in solid form from Edward Mendell Co., Inc.. Six tablets including each of the three lubricants/aids were tested and the averages taken and disintegration was measured in 0.1N HCL at 37 degrees C. As FIG. 1 illustrates the disintegration properties of the tableting aid of the present invention maintains a substantially constant as concentrations vary between 0.5 and 1.5 weight percent based on the overall weight of the tablet. In all cases, disintegration occurred in less than 5 minutes. While tablets including LUBRITAB dissolved in less time than the tablets including tableting aid of the present invention at concentrations of 0.5 percent, as concentration increased, the disintegration time of the LUBRITAB containing tablets increased dramatically such that at a concentration of 1.5 percent, the disintegration time increased to in excess of 15 minutes. In all concentrations tested magnesium stearate took in excess of 60 minutes to disintegrate, and therefore cannot be shown on the graph.

EXAMPLE XII

With reference to FIG. 2 the effect of lubricant concentration on the hardness of directly compressible calcium carbonate was determined and is graphically represented. 20 tablets of each of the three additives described in Example XI were used to determine the average for each data point and tablets were prepared as in Example XI. Tablets containing LUBRITAB demonstrated superior hardness as the percent of lubricant in the tablets increased from 0.5 to 1.5 weight percent. The tablets containing the tableting aid of the present invention also showed acceptable hardness. Magnesium stearate possessed the lowest overall hardness and showed a maximum hardness at a concentration of 1 percent. As concentration increased beyond 1 percent hardness of tablets produced thereby decreased.

EXAMPLE XIII

With reference to FIG. 3 the effect of the lubricant concentration on the friability of directly compressible calcium carbonate was measured and is graphically represented therein.

Friability is a measure of a tablet's ability to withstand the physical trauma encountered in handling, such as during counting, packaging, or shipping. Friability is measured by placing 10 tablets into a friabilator after having first determined the weight of the tablets. The tablets are then rotated in the friabilator for 100 rotations and t he final tablet weight is determined. The tablet's hardness and structural integrity are related to the amount of weight loss with a lower weight loss equating to a harder tablet. Friability equals the difference between the initial weight of the tablet and the final weight, divided by the initial weight with the remainder multiplied by 100. Thus the higher the weight loss, the higher the percentage friability. Tablets were prepared as in Example XII.

Tablets containing LUBRITAB exhibit a decrease in the percent friability as the concentration of lubricant increases. Thus at higher concentrations, LUBRITAB may produce tablets of superior hardness. The opposite is true of magnesium stearate. At a concentration of 0.5 percent, tablets containing magnesium stearate have a percent friability approximately equal to tablets prepared with the tableting aid of the present invention. However, as the concentration of magnesium stearate increases, the percent friability of the tablets produced dramatically increase. Tablets including the tableting aid of the present invention, also referred to as TA, show a more consistent substantially constant percent friability as the concentration of lubricant increases. Thus, unlike LUBRITAB and magnesium stearate, the tableting aid of the present invention provides acceptable friability throughout the entire range of concentrations tested.

With reference to FIG. 4 the effect of lubricant blending time on the hardness of directly compressible calcium carbonate was determined and is graphically represented. The lubricant concentration remained constant at 1 percent. However, the remaining parameters were identical to those in Example XII. As will be readily appreciated the hardness of tablets containing LUBRITAB was highest over the complete range of blend times from 5 to 15 minutes. Blend time is understood to mean the amount of time that a lubricant is blended with an intended ingredient and/or other ingredients prior to tableting. The tablets containing the tableting aid of the present invention possessed a more linear progression over blend time but at a lower degree of hardness throughout the entire blend time range tested. Magnesium stearate exhibited the lowest level of hardness overall and the hardness of tablets dropped dramatically as blend time exceeded 10 minutes.

EXAMPLE XV

With reference to FIG. 5 the effect of the lubricant blending time on the disintegration time of directly compressible calcium carbonate was determined and is graphically represented. In all cases a percent lubricant concentration was used. The remaining parameters are equivalent to those discussed in Example XII. Tablets containing the tableting aid of the present invention retained a relatively flat, linear behavior with regard to the relationship of disintegration time and blend time. In all cases the disintegration time of tablets produced with the tableting aid of the present invention remained under 5 minutes. However, blend time has a dramatic effect on the disintegration rate of tablets produced with LUBRITAB. When LUBRITAB is blended for 5 minutes with the intended ingredients, the disintegration time of the tablet produced is 3 times that of the tablet using the tableting aid of the present invention. When blend time is extended to 15 minutes disintegration time of a tablet produced with LUBRITAB is between about 20 and 25 minutes. All the tablets including magnesium stearate disintegrated in excess of 60 minutes.

EXAMPLE XVI

Figure 6:
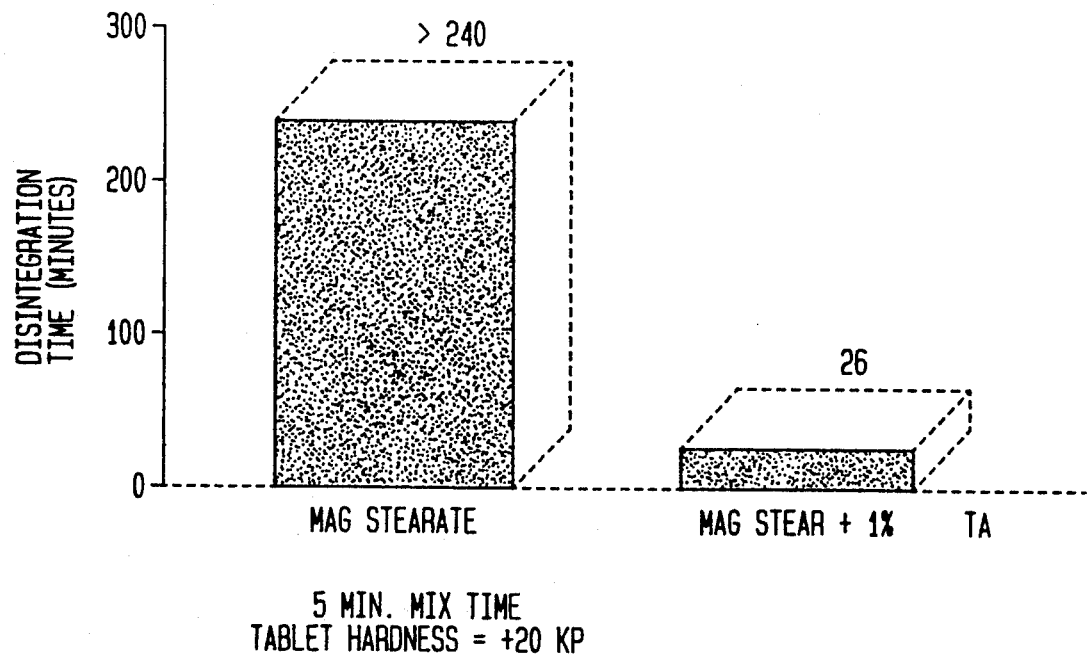
FIG. 6 is a graphical representation of the effect of the tableting aid or TA of the present invention, in combination with magnesium stearate on the disintegration time of directly compressible calcium carbonate.

With reference to FIG. 6 the effect of the addition of the tableting aid of the present invention to a tablet containing 0.5 percent magnesium stearate on the disintegration time of directly compressible calcium carbonate was measured and is graphically represented. Tablets containing only magnesium stearate as a lubricant for calcium carbonate required 240 minutes to completely disintegrate. The addition of only 1 percent of the tableting aid of the present invention reduced the disintegration time of a tablet produced thereby to 26 minutes even though the same amount of magnesium stearate was still present in these tablets.

EXAMPLE XVII

With reference to FIG. 7 the effect of lubricant blending time on the disintegration time of AVICEL (AVICEL is a registered trademark of FMC Corporation) tablets was determined and is graphically represented. 500 mg of AVICEL was blended with 5.0 mg of either magnesium stearate on TA, the tableting aid of the present invention. The mixtures were blended for either 5 minutes or 20 minutes in a low speed mixer and then tableted in accordance with the procedures of EXAMPLE VII. Three tablets of each were prepared. Disintegration was measured at 37 degrees C in distilled water.

|  | T1 mg/tab | T2 mg/tab |
|---|---|---|
| AVICEL | 500.0 | 500.0 |
| Magnesium Stearate | 5.0 | — |
| TA* | — | 5.0 |
| Tablet weight | 505.0 | 505.0 |

*Magnesium carbonate tableting aid formed in accordance with Example II.

The average disintegration time of 3 tablets of formulation T1 blended for 5 minutes was 7.0 minutes.

The average disintegration time of 3 tablets of formulation T1 blended for 20 minutes was 35.5 minutes.

The average disintegration time of 3 tablets of formulation T2 blended for 5 minutes was 4.5 minutes.

The average disintegration time of 3 tablets of formulation T2 blended for 20 minutes was 5.1 minutes.

As illustrated by FIG. 7, magnesium stearate is very sensitive to blend time and disintegration time increases with blend time. The tableting aid of the present invention, however, retains a substantially constant disintegration time throughout the entire range of tested blend times.

AVICEL is a popular tableting binder which when used, generally requires the use of disintegrant and a lubricant. However, by using the tableting aid of the present invention, the need to include both additives is eliminated. Beside the obvious economic and compatibility advantages, the reduction in the number of ingredients can allow for a reduction in the weight and size of a tablet. This may be particularly important when preparing tablets for those who are uncomfortable about ingesting large tablets.

EXAMPLE XVIII

With reference to FIG. 8, the effect of TA, the tableting aid of the present invention, on the disintegration of AVICEL tablets containing 1.0 percent magnesium stearate was measured and is graphically represented. Tablets of AVICEL were prepared by blending 500 mg of AVICEL with 5 mg of each of magnesium stearate and TA. Mixing was at a low speed for 20 minutes. Tablets disintegrated in an average of 5.8 minutes. When compared to the average disintegration time of AVICEL tablets containing only magnesium stearate as prepared and tested in Example XVII, tablets containing both additives disintegrated on an average of six times faster.

No one lubricant or disintegration agent provides the perfect solution to every parameter tested. However, unlike the tableting aids of the prior art, the tableting aid of the present invention provides acceptable and often superior hardness, superior lubrication properties and vastly superior disintegration properties without being sensitive to concentration, blend time, and the like. Thus the tableting aid of the present invention provides an extremely versatile and useful product which maximizes the advantageous properties which are desirable while minimizing foreseeable disadvantages.

EXAMPLE XIX

The relative ability of calcium carbonate and magnesium carbonate to adsorb flavor oil and the characteristics of the resulting carrier and oil products were observed. One hundred and fifty grams of precipitated heavy calcium carbonate powder U.S.P. (Pfizer, Lot No. A8354-2) and one hundred and fifty grams of magnesium carbonate, heavy U.S.P. (Whittaker, Clark & Daniels, Lot No. H83) were weighed out. One hundred and fifty grams of Oil Lemon Calif., 5-fold extra (Citrus & Allied, Lot No. 16392) were measured and placed into separate beakers. The calcium carbonate was charged into a four quart KITCHEN-AID mixer and mixed at low speed. The flavor oil was slowly added until adsorption capacity was reached. "Adsorption" capacity as used herein refers to the point at which further addition of oil would result in granulation and very poor or non-existent flowability. The amount of oil used to reach the adsorption capacity was then recorded. The material was screened through a Number 16 screen and the procedure was repeated for magnesium carbonate.

| Material | Grams of Oil to Reach Adsorption Capacity | Weight % of Oil Adsorbed |
|---|---|---|
| Calcium Carbonate | 20 | 11.7 |
| Magnesium Carbonate | 118 | 44.0 |

The calcium carbonate and oil product forms agglomerates and exhibits very poor flowability. The free-flowing property of a calcium carbonate and flavor oil mixture was compromised significantly before the adsorption capacity was reached. In contrast, magnesium carbonate adsorbed about four times the amount of flavor oil that calcium carbonate was able to adsorb, and the resulting powder remained discreet and retained good free-flow characteristics. Additional oil could be added to the magnesium carbonate, up to between about 50 and about 55% oil by weight while still retaining acceptable free-flow characteristics for certain applications.

The principles, preferred embodiments, and modes of operation of the present invention have been described in the foregoing specification. The invention which is intended to be protected herein, however, is not to be construed as limited to the particular embodiments disclosed, since these are to be regarded illustrative rather than restrictive. Variations and changes may be made by others without departing from the spirit and scope of the invention.

One such variation involves preparation of capsules. In capsule filling, a powder composition may be compressed, typically within a small tube or bore commonly referred as a filling chamber or cavity, to form a slug. The slug may be inserted in a capsule shell, as by ejecting the slug from the filling chamber or cavity into the capsule shell. The terms "tablet" and "tableting" as used in this disclosure should be understood as including such a slug and formation of such a slug.

What is claimed is:

1. A process of producing a tablet comprising the steps of:
    forming a tableting composition by blending at least one active ingredient and a particulate tableting aid comprising particulate magnesium carbonate having adsorbed thereon, at least one oil, said oil being present in an amount effective to produce a dry free-flowing, dry particulate tableting aid wherein the ratio of said oil to said magnesium carbonate is between about 0.15:1 and about 0.6:1 by weight; and
    forming a tablet by the application of compressive forces to the tableting composition, said tableting aid effectively lubricating the tablet during said forming step.

2. The process of producing a tablet of claim 1 wherein said composition further includes at least one additional adjuvant selected from the group consisting of flavors, diluents, colors, binders, disintegration agents, lubricants and effervescent agents.

3. A tablet produced by the process of claim 1.

4. A tablet produced by the process of claim 2.

5. The process of producing a tablet of claim 1 wherein, the ratio of said oil of said magnesium carbonate is between about 0.25:1 and about 0.45:1 by weight.

6. The process of producing a tablet of claim 1 wherein said particulate tableting aid is present in an amount greater than 0% and less than about 20% by weight of the total composition.

7. The process of producing a tablet of claim 6 wherein said particulate tableting aid is present in an amount from greater than 0% to about 2.0% by weight of the total composition.

8. The process of producing a tablet of claim 7 wherein said particulate tableting aid is present in an amount of between about 0.1% to about 1.5% by weight of the total composition.

9. The process of producing a tablet of claim 7 wherein the ratio of said oil to said magnesium carbonate in said particulate tableting aid is between about 0.15:1 and about 0.6:1 by weight and said particulate tableting aid is present in an amount greater than 0% and less than about 20% by weight of the total composition.

* * * * *

UNITED STATES PATENT AND TRADEMARK OFFICE
CERTIFICATE OF CORRECTION

PATENT NO. : 5,219,574

DATED : June 15, 1993

INVENTOR(S) : Wehling, et al.

It is certified that error appears in the above-identified patent and that said Letters Patent is hereby corrected as shown below:

Column 8, line 47, cancel "10".
Column 9, line 29, "I" should read --1--.
Column 11, line 37, "I" should read --1--.
Column 19, line 63, "t he" should read --the--.
Column 24, line 6, "of" should read --to--.

Signed and Sealed this

Twenty-sixth Day of April, 1994

Attest:

BRUCE LEHMAN

Attesting Officer  Commissioner of Patents and Trademarks